United States Patent
Dasbach et al.

(10) Patent No.: US 9,393,360 B2
(45) Date of Patent: Jul. 19, 2016

(54) NEEDLE ASSEMBLY STORAGE DEVICE

(75) Inventors: Uwe Dasbach, Frankfurt am Main (DE);
Verena Hofmann, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 317 days.

(21) Appl. No.: 14/004,109

(22) PCT Filed: Mar. 9, 2012

(86) PCT No.: PCT/EP2012/054102
§ 371 (c)(1),
(2), (4) Date: Sep. 9, 2013

(87) PCT Pub. No.: WO2012/123354
PCT Pub. Date: Sep. 20, 2012

(65) Prior Publication Data
US 2013/0341224 A1 Dec. 26, 2013

(30) Foreign Application Priority Data
Mar. 15, 2011 (EP) .................................... 11158262

(51) Int. Cl.
*A61M 5/00* (2006.01)
*A61M 5/32* (2006.01)

(52) U.S. Cl.
CPC .............. *A61M 5/002* (2013.01); *A61M 5/3205* (2013.01); *A61M 2005/3208* (2013.01); *A61M 2205/581* (2013.01); *A61M 2205/582* (2013.01)

(58) Field of Classification Search
CPC .... B65D 83/02; A61M 5/002; A61M 5/3205; A61M 2005/3208; A61M 2205/582; A61B 19/0262
USPC .................. 206/366, 363, 365, 364; 604/198
See application file for complete search history.

(56) References Cited

U.S. PATENT DOCUMENTS

| | | | | |
|---|---|---|---|---|
| 5,873,462 A | * | 2/1999 | Nguyen | A61M 5/002 206/366 |
| 5,968,021 A | * | 10/1999 | Ejlersen | A61M 5/3213 206/365 |
| 5,971,966 A | * | 10/1999 | Lav | A61M 5/002 206/365 |
| 6,346,094 B2 | | 2/2002 | West et al. | |
| 7,370,759 B2 | | 5/2008 | Hommann | |
| 9,016,472 B2 | * | 4/2015 | Van der Beek | A61M 5/002 206/366 |
| 2002/0014430 A1 | * | 2/2002 | Groth | A61M 5/002 206/438 |
| 2005/0271465 A1 | | 12/2005 | Lehmann | |
| 2009/0069753 A1 | * | 3/2009 | Ruan | A61M 5/3202 604/192 |
| 2012/0037655 A1 | * | 2/2012 | DiBiasi | A61M 5/008 221/1 |
| 2012/0041380 A1 | * | 2/2012 | Chapin | A61M 5/002 604/192 |

FOREIGN PATENT DOCUMENTS

| | | |
|---|---|---|
| EP | 0990446 A1 | 4/2000 |
| EP | 1567209 B1 | 11/2003 |
| EP | 1567215 B1 | 11/2003 |

* cited by examiner

Primary Examiner — Steven A. Reynolds
(74) Attorney, Agent, or Firm — Fish & Richardson P.C.

(57) ABSTRACT

Described is a needle assembly storage device. The storage device includes a container, a pocket formed in the container adapted to receive a needle assembly, and a pull linkage connecting the needle assembly to the container. The pull linkage disengages the needle assembly when sufficient rotational force has been applied to the needle assembly in a first direction. A projection on the needle assembly prevents rotation of the needle assembly in the pocket in a second rotation direction opposite to the first direction.

18 Claims, 5 Drawing Sheets

NEEDLE ASSEMBLY STORAGE DEVICE

CROSS REFERENCE TO RELATED APPLICATIONS

The present application is a U.S. National Phase Application pursuant to 35 U.S.C. §371 of International Application No. PCT/EP2012/054102 filed Mar. 9, 2012, which claims priority to European Patent Application No. 11158262.3 filed Mar. 15, 2011. The entire disclosure contents of these applications are herewith incorporated by reference into the present application.

FIELD OF INVENTION

The invention relates to a storage device for needle assemblies.

BACKGROUND

Conventional injection device include a distal end for receiving single-use needle assemblies. Typically, a user will attach a needle assembly to the injection device (e.g., by a threaded connection) and remove the needle assembly after an injection has been administered. Removal of the needle assembly from the injection device bears the risk of injury (e.g., needle-stick) to the user. Therefore, various devices have been proposed to reduce this risk of injury.

Further, when attaching the needle assembly to the injection device, an appropriate amount of torque is necessary. However, application of torque beyond the appropriate amount may result in overtightening (preventing removal of the needle assembly), fracture of the needle assembly and/or injection device, and/or injury to the user.

EP 1567209 B1 discusses a device for removing and replacing a needle cover. EP 1567215 B1 discusses a device for making and/or tightening fluid-guiding threaded connections, including Luer-lock type connections,

SUMMARY

It is an object of the present invention to provide an improved needle assembly storage device.

In an exemplary embodiment of the present invention, a needle assembly storage device comprises a container and a pocket formed in the container for receiving a needle assembly. The needle assembly may comprise a needle and a housing for receiving an injection device. The device further comprises a pull linkage connecting the needle assembly to the container. The pull linkage disengages the needle assembly when sufficient rotational force has been applied to the needle assembly in a first direction. A projection on the needle assembly prevents rotation of the needle assembly in the pocket in a second rotation direction opposite to the first direction.

In an exemplary embodiment, the needle assembly includes a screw thread for coupling to the injection device. The screw thread may be an internal thread on an inner surface of the needle assembly. The projection may prevent rotation of the needle assembly within the pocket in the second direction when the projection abuts the pull linkage. The projection may have a first leg extending perpendicular to a tangent of an outer border of the needle assembly and a second leg as a sloped surface between the first leg and the outer border.

In an exemplary embodiment, a peelable film may cover an opening of the needle assembly when the needle assembly is in the pocket.

In an exemplary embodiment, the needle assembly comprises an annular collar to bear on a surface of the container. The pull linkage may include a sloped surface having a first end and a second end. Rotation of the needle assembly in the first direction generates resistance when the projection abuts the pull linkage.

In an exemplary embodiment, a first tactile feedback is provided when the projection bypasses the pull linkage when the needle assembly is rotated in the first direction. A second tactile feedback may be provided when the projection abuts the pull linkage when the needle assembly is rotated in the second direction.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given below and the accompanying drawings wherein.

Corresponding parts are marked with the same reference symbols in all figures.

DETAILED DESCRIPTION

Figure 1:
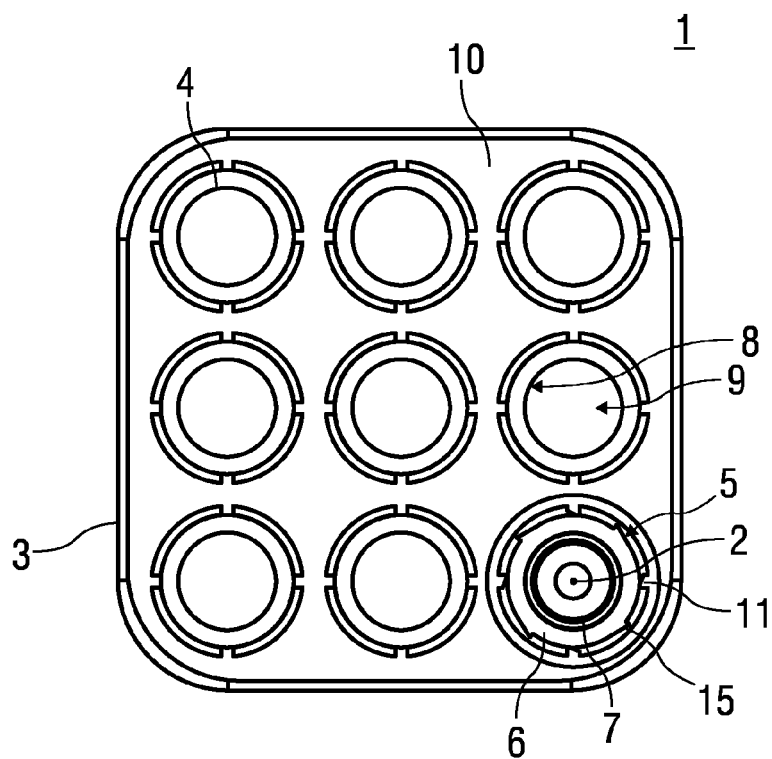
FIG. 1 shows a top view of an exemplary embodiment of a needle assembly storage device according to the present invention.
Figure 2:
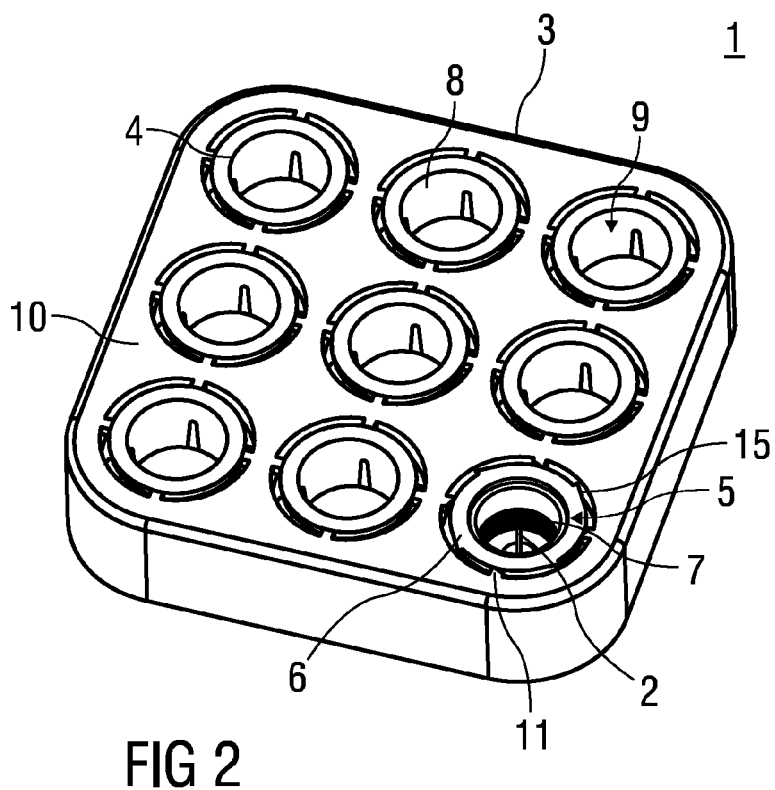
FIG. 2 shows a perspective view of an exemplary embodiment of a needle assembly storage device according to the present invention.

FIGS. 1 and 2 show a top view and a perspective view of an exemplary embodiment of a needle assembly storage device 1 for needle assemblies 5, respectively. The storage device 1 comprises a container 3 with one or more pockets 4. Each pocket 4 may be sized and shaped to receive a needle assembly 5. In the exemplary embodiments shown in FIG. 1, needle assemblies 5 are received in each of the pockets 4. Those of skill in the art will understand that the container 3 may be any size and/or shape (e.g., linear, box, etc.) and contain any number of pockets 4. Prior to use, when the needle assembly 5 is received in one of the pockets 4, the pocket 4 may be covered with a peelable film (not shown) or other device for maintaining a sterility of the needle assembly 5. The peelable film may cover an opening of the needle assembly 5 into which the injection device will be inserted for coupling thereto. The peelable film may be coupled to the pocket 4 by, for example, an adhesive.

Each needle assembly 5 is sized and shaped to be received in one of the pockets 4. In an exemplary embodiment, the needle assembly includes a cylindrical housing having an inner threaded surface 7 for engaging a threaded end of an injection device and a double-pointed needle 2. In an exemplary embodiment, the needle assembly 5 has the shape of a cylindrical brimmed hat, with a top cover which the needle 2 protrudes through along a longitudinal axis of the needle assembly 5, and with a brim formed as an annular collar 6. In an exemplary embodiment, the threaded surface 7 is right-handed, although in other embodiments, the threaded surface 7 may be left-handed.

Each pocket 4 of the container 3 has a cylindrical wall 8 with a container-sided end defining the contour of a circular opening 9 in a surface 10 of the container 3. The inner diameter of the cylindrical wall 8 extends slightly the outer diameter of the cylindrical part of the needle assembly 5 so that the pocket 4 can receive a needle assembly 5. Furthermore the outer diameter of the annular collar 6 extends the diameter of the circular opening 9 so that the annular collar 6 of a needle assembly 5 received in the pocket 4 bears on a surface surrounding the circular opening 9.

Figure 3:
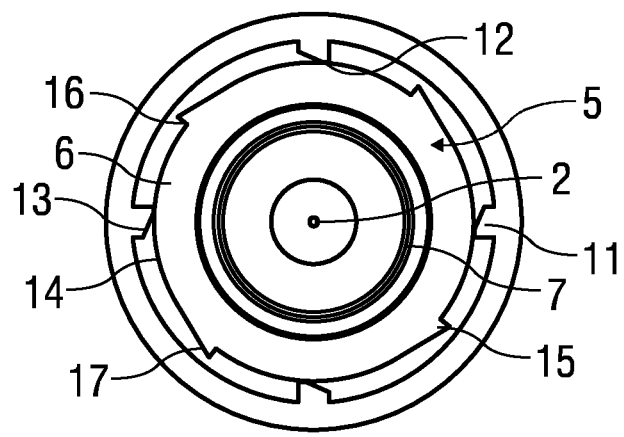
FIG. 3 shows a top view of a needle assembly within a pocket of an exemplary embodiment of a needle assembly storage device according to the present invention.

As shown in more detail in FIG. 3, in an exemplary embodiment, each needle assembly 5 is connected to the container 3 by one or more pull linkages 11. A first end of each pull linkage 11 is connected to (or formed integrally with) the container 3, and a second end of each pull linkage 11 comprises a first end portion 12 which is connected to a needle assembly 5 and defines a predetermined breaking point between the pull linkage 11 and the needle assembly 5. A second end portion 13 of the second end of each pull linkage 11 adjoins the first end portion 12 and is angled radially away from a circumference of the needle assembly 5. Along the contour of the circular opening 9, the first and second end portions 12, 13 of the pull linkages 11 alternate so that the first end portion 12 of each pull linkage 11 faces the second end portion 13 of a neighbouring pull linkage 11.

In an exemplary embodiment, the outer border 14 of the annular collar 6 of the needle assembly 5 includes at least one projection 15. In an exemplary embodiment in which there are multiple projections 15, the projections 15 may be placed at equal distances along the outer border 14 and correspond to the number of pull linkages 11 connected to the respective needle assembly 5. The projection 15 may have a shape of a triangle with a first leg 16 formed perpendicular to a tangent of the outer border 14 and a second leg 17 having a sloped decline into the outer border 14. In the exemplary embodiment, when the needle assembly 5 is turned in a first direction within the pocket 4, the first end 12 of the pull linkage 11 may follow (e.g., in contact) along the outer border 14, and resistance may be felt as the second leg 17 comes into contact with the first end 12 and second end 13 of the pull linkage 11. The resistance may increase until the projection 15 bypasses the first end 12 of the pull linkage 11, at which point the user may be provided with a tactile feedback, e.g., a sudden decrease in the resistance.

FIGS. 1 to 3 show an exemplary embodiment of a needle assembly 5 in its initial position within the pocket 4 before a distal end of an injection device is coupled to the needle assembly 5. When the distal end of the injection device is inserted into the needle assembly 5, the injection device may be rotated in a first direction, e.g., clockwise, to secure the needle assembly 5 thereto. The pull linkages 11 prevent the needle assembly 5 from rotating within the pocket 4 as it is being secured to the injection device. When the needle assembly 5 has been properly secured to the injection device, further rotation in the first direction of the needle assembly 5 may result in a disengagement of the pull linkages 11 from the outer border 14 of the needle assembly 5. Thus, further rotation of the injection device in the first direction will not result in further tightening of the needle assembly 5 thereto. Also, the disengagement of the pull linkage 11 may provide a tactile (and/or audible) feedback to the user. That is, while securing the injection device to the needle assembly 5, the user may feel resistance while the pull linkages 11 secure the container 3 to the needle assembly 5. When a sufficient amount of torque is applied and the needle assembly 5 disengages from the pull linkages 11, the user may feel a sudden decrease in resistance to further rotation of the injection device.

Figure 4:
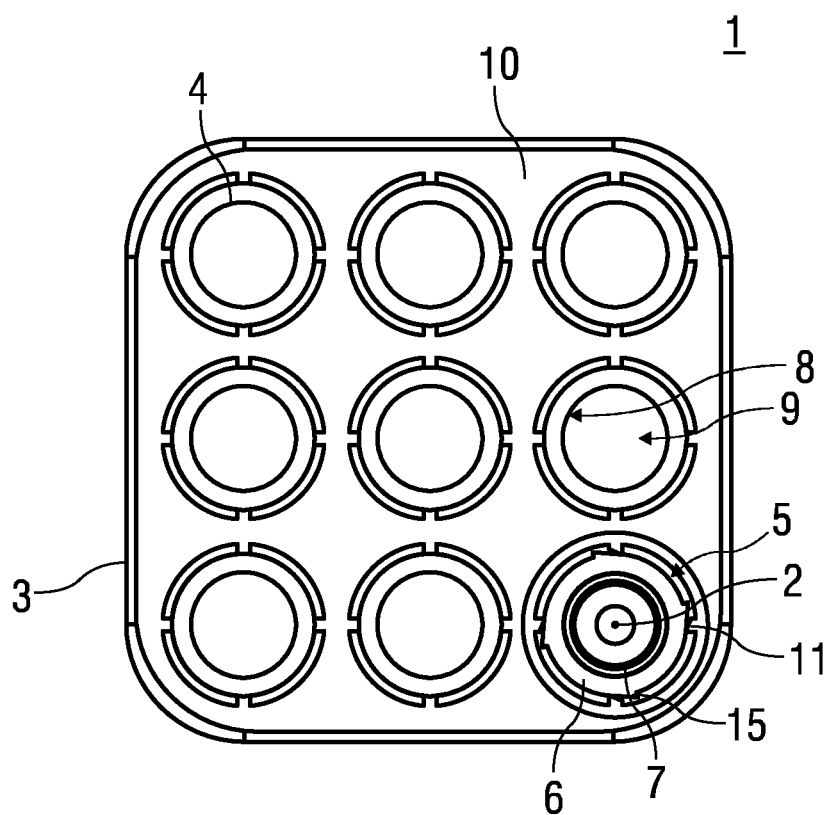
FIG. 4 shows a top view of an exemplary embodiment of a needle assembly storage device according to the present invention.
Figure 5:
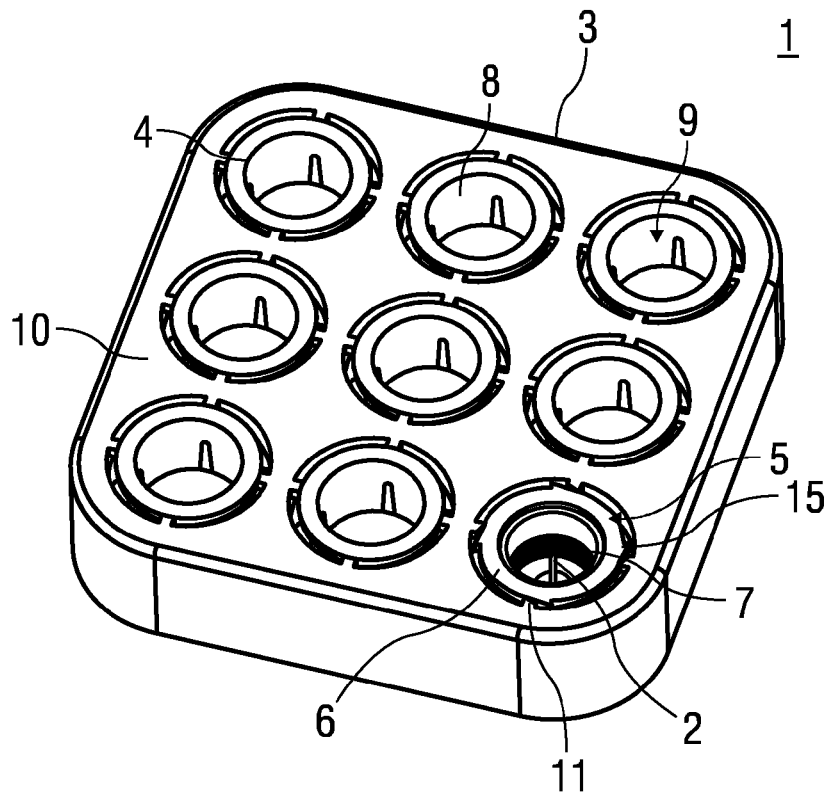
FIG. 5 shows a perspective view of an exemplary embodiment of a needle assembly storage device according to the present invention.

FIGS. 4 and 5 show an exemplary embodiment of the storage device 1 of FIGS. 1 and 2 after the injection device has been secured to the needle assembly 5 and the pull linkages 11 have been disengaged. In this state, the needle assembly 5 is mounted on the injection device can be rotated freely (e.g., in the first direction) in the pocket 4 and removed from the pocket 4 so that the injection device with the needle assembly 5 mounted on it is ready for use.

Figure 6:
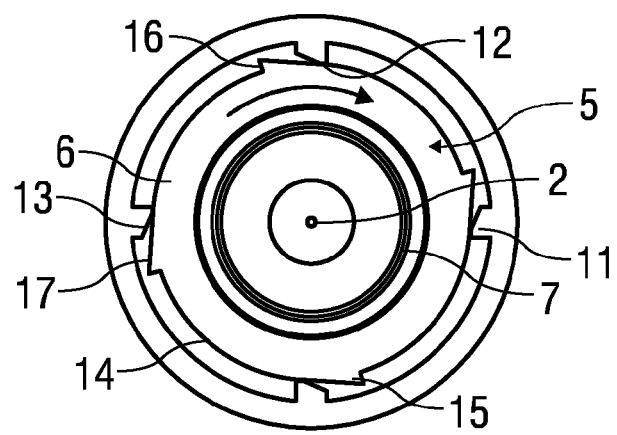
FIG. 6 shows a top view of a needle assembly within a pocket of an exemplary embodiment of a needle assembly storage device according to the present invention.

FIG. 6 shows in more detail a top view of an exemplary embodiment of the needle assembly 5 within the pocket 4 in this state. The arrow in the exemplary embodiment shown in FIG. 6 shows a first direction (clockwise in the figure) in which the needle assembly 5 may freely rotate within the pocket 4 without further tightening the needle assembly 5 to the injection device. However, in an exemplary embodiment, further rotation of the needle assembly 5 in the first direction may cause the user to feel resistance as the second leg 17 of the projection 15 abuts the first and second ends 12, 13 of the pull linkage 11. The resistance may increase as the needle assembly 5 is rotated until the projection 15 bypasses the first end 12 of the pull linkage 11.

After administering an injection, the needle assembly 5 mounted on the injection device may be reinserted into the pocket 4.

Figure 7:
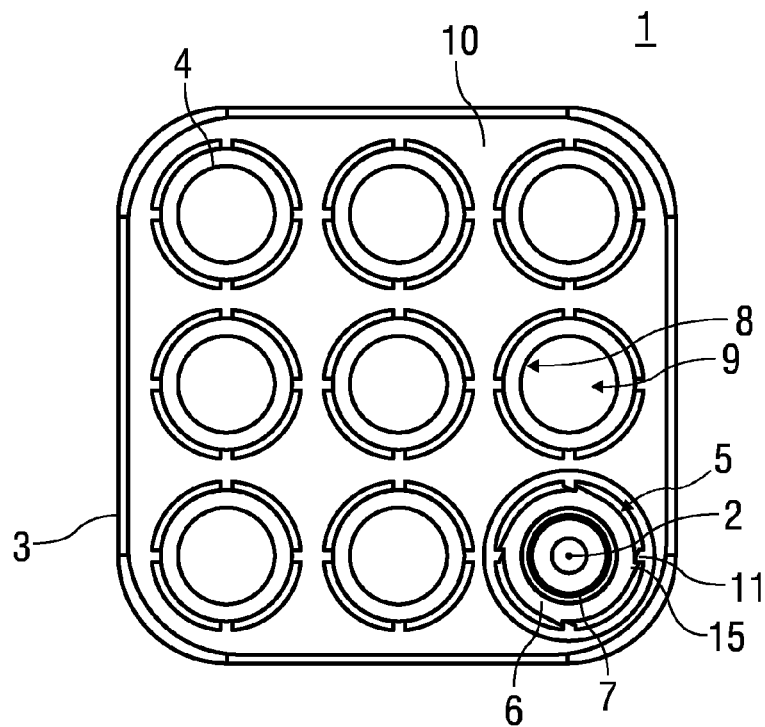
FIG. 7 shows a top view of a needle assembly within a pocket of an exemplary embodiment of a needle assembly storage device according to the present invention.
Figure 8:
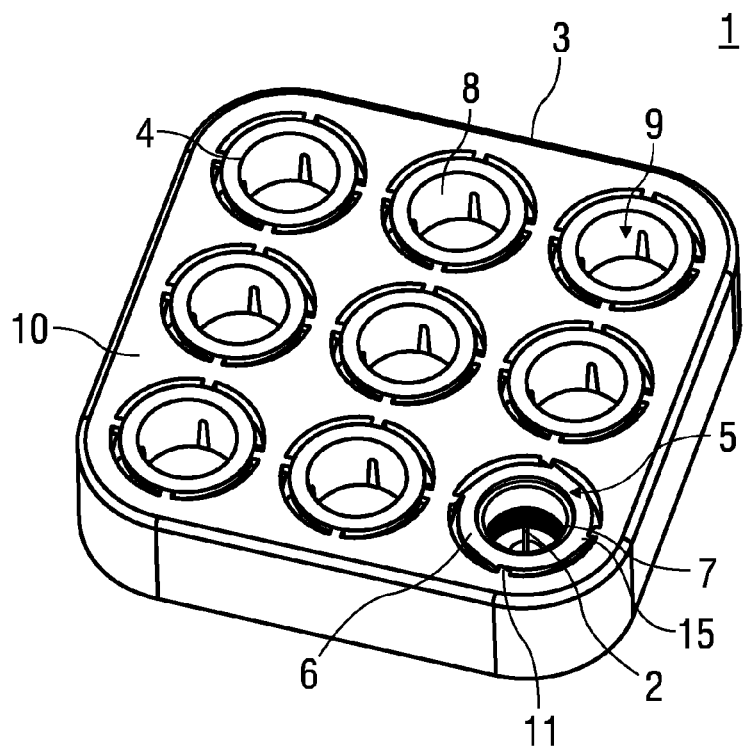
FIG. 8 shows a perspective view of an exemplary embodiment of a needle assembly storage device according to the present invention.
Figure 9:
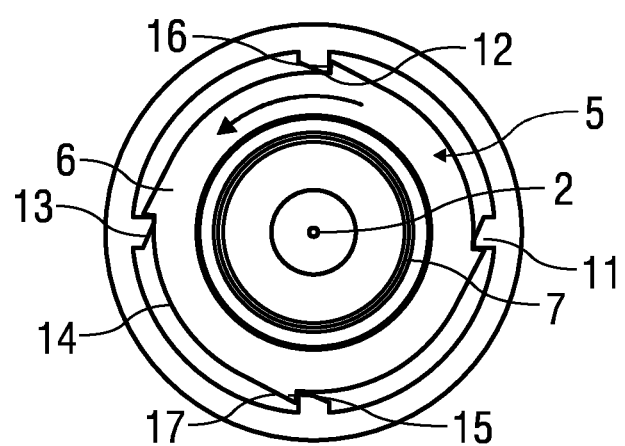
FIG. 9 shows a top view of a needle assembly within a pocket of an exemplary embodiment of a needle assembly storage device according to the present invention.

FIGS. 7 to 9 show how the needle assembly 5 may be removed from the injection device after the injection has been administered. In an exemplary embodiment, the needle assembly 5 is reinserted into the pocket 4 (not necessarily the same pocket 4 from which it was removed). To remove the needle assembly 5 from the injection device, the injection device (and thus the needle assembly 5 secured thereto) is turned in a second direction (e.g., counter-clockwise). When the first leg 16 of the projection 15 abuts the first end 12 of the pull linkage 11, further rotation of the needle assembly 5 in the second direction is prevented. However, the injection device may continue to rotate in the second direction until it disengages the needle assembly 5.

After a needle assembly 5 has been separated from the container and reinserted into a pocket 4, it may difficult to remount that needle assembly 5 on the injection device, because the needle assembly 5 will be free to rotate within the pocket 4 as the injection device attempts to engage the needle assembly 5. Such a configuration may discourage reuse of previously used needle assemblies 5.

Those of skill in the art will understand that other exemplary embodiments of the invention use different numbers, geometries, alignments and/or orientations of the pull linkages 11 and/or the projections 15. Furthermore, one may use left-handed in place of right-handed screw threads 7 and correspondingly amended embodiments of projections 15 which prevent clockwise turnings of a needle assembly 5 within a pocket 4.

The invention claimed is:

1. A needle assembly storage device, the storage device comprising:
   a container;
   a pocket formed in the container;
   a needle assembly received in the pocket;
   a pull linkage comprising an end portion defining a predetermined breaking point connecting the needle assembly to the container, the predetermined breaking point being configured to break to disconnect the needle assembly from the container when a sufficient rotational force is applied to the needle assembly in a first direction; and
   a projection on the needle assembly configured to limit rotation of the needle assembly in the pocket in a second direction opposite to the first direction when the pull linkage is disengaged from the needle assembly.

2. The storage device according to claim 1, wherein the needle assembly includes a screw thread configured to couple the needle assembly to an injection device when the screw thread is engaged with the injection device and the injection device is rotated in the first direction.

3. The storage device according to claim 2, wherein the screw thread is an internal thread on an inner surface of the needle assembly.

4. The storage device according to claim 1, wherein the projection is configured to limit rotation of the needle assembly within the pocket in the second direction when the projection abuts the pull linkage.

5. The storage device according to claim 1, wherein the projection has a first leg extending perpendicular to a tangent of an outer border of the needle assembly and a second leg as a sloped surface between the first leg and the outer border.

6. The storage device according to claim 1, wherein a peelable film covers an opening of the needle assembly when the needle assembly is in the pocket.

7. The storage device according to claim 1, wherein the needle assembly comprises an annular collar to bear on a surface of the container.

8. The storage device according to claim 1, wherein the pull linkage includes a sloped surface having a first end and a second end, the first end being connected to the container, and the second end defining the predetermined breaking point connecting the needle assembly and the container.

9. The storage device according to claim 1, wherein the projection is configured such that rotation of the needle assembly in the first direction generates resistance when the projection abuts the pull linkage.

10. The storage device according to claim 1, wherein the projection is configured to generate a first tactile feedback when the projection bypasses the pull linkage when the needle assembly is rotated in the first direction.

11. The storage device according to claim 10, wherein the projection is configured to generate a second tactile feedback when the projection abuts the pull linkage when the needle assembly is rotated in the second direction.

12. The storage device according to claim 1, wherein the predetermined breaking point and the pull linkage is integrally formed with the container.

13. The storage device according to claim 1, wherein the projection is configured to abut the pull linkage when the predetermined breaking point breaks and to limit rotation of the needle assembly within the pocket in the second direction when the projection abuts the pull linkage.

14. The storage device according to claim 1, wherein the pocket and the needle assembly are a first pocket and a first needle assembly, respectively, and the storage device further comprises a second pocket formed in the container and a second needle assembly received in the second pocket.

15. The storage device according to claim 1, wherein:
   the pull linkage is a first pull linkage,
   the storage device comprises a second pull linkage connecting the needle assembly to the container, and
   the projection is disposed between the first pull linkage and the second pull linkage.

16. The storage device according to claim 15, wherein:
   the projection is configured to abut the first pull linkage when the needle assembly is rotated in the second direction and to limit rotation of the needle assembly within the pocket in the second direction when the projection abuts the first pull linkage, and
   the projection is further configured to contact the second pull linkage when the needle assembly is rotated in the first direction and to generate a resistance to rotation of the needle assembly in the first direction when the projection abuts the second pull linkage.

17. The storage device according to claim 1, wherein the pull linkage is one of a plurality of pull linkages equally spaced along a circumference of the needle assembly.

18. The storage device according to claim 1, wherein the needle assembly is configured to be secured to an injection device through rotation of the injection device relative to the needle assembly in the first direction, the rotation of the injection device applying a rotational force to the needle assembly less than the sufficient rotational force.

* * * * *